United States Patent [19]

Golden

[11] Patent Number: 4,846,176
[45] Date of Patent: Jul. 11, 1989

[54] THERMAL BANDAGE

[76] Inventor: Theodore A. Golden, 762 Wooddale Rd., Birmingham, Mich. 48010

[21] Appl. No.: 18,115

[22] Filed: Feb. 24, 1987

[51] Int. Cl.$^4$ ............................................. A61F 7/00
[52] U.S. Cl. ................................ 128/400; 128/379; 128/384; 165/46
[58] Field of Search ............... 128/384, 400, 399, 403, 128/402; 165/46; 62/530, 437, 438, 439

[56] References Cited

U.S. PATENT DOCUMENTS

| | | | |
|---|---|---|---|
| 1,896,953 | 2/1933 | Hassell | 128/400 |
| 2,595,328 | 5/1952 | Bowen | 128/403 |
| 2,726,658 | 12/1955 | Chessey | 128/400 |
| 3,133,539 | 5/1964 | Eidus | 128/399 |
| 3,202,801 | 8/1965 | Saluri | 128/399 |
| 3,683,902 | 8/1972 | Artemenko | 128/400 |
| 3,738,367 | 6/1973 | Hardy | 128/400 |
| 3,865,116 | 2/1975 | Brooks | 128/400 |
| 3,885,403 | 5/1975 | Spencer | 128/399 |
| 4,098,279 | 7/1978 | Golden | 128/400 |
| 4,108,146 | 8/1978 | Golden | 128/400 |
| 4,483,021 | 11/1984 | McCall | 128/399 |
| 4,640,284 | 2/1987 | Ruderian | 128/399 |

FOREIGN PATENT DOCUMENTS

| | | | |
|---|---|---|---|
| 3238425 | 4/1984 | Fed. Rep. of Germany | 128/400 |
| 1262837 | 4/1961 | France | 128/400 |
| 2491331 | 4/1982 | France | 128/402 |
| 2093981 | 9/1982 | United Kingdom | 165/46 |

Primary Examiner—Richard C. Pinkham
Assistant Examiner—Mark S. Graham
Attorney, Agent, or Firm—Ralph T. Rader

[57] ABSTRACT

A thermal bandage including a conforming member which is adapted to be placed against the skin to uniformly heat or cool the skin area, a thermal pack which is mounted to the conforming member to provide the necessary thermal change to heat or cool the adjacent skin area and the thermal conducting surface interposed between the conforming member and a thermal pack to separate them and to facilitate heat transfer between them. In the preferred embodiment, the conforming member has a thin pliable outer material enclosing a heat conductive substance such as a glycol gel or liquid. The conductive substance readily conforms to the contours of the body portion so that the conforming members is in complete contact with the skin to insure uniform heat transfer therebetween. The thermal pack of the preferred embodiment is flexible and has a fluid flow chamber therein for the circulation of a thermal fluid.

8 Claims, 3 Drawing Sheets

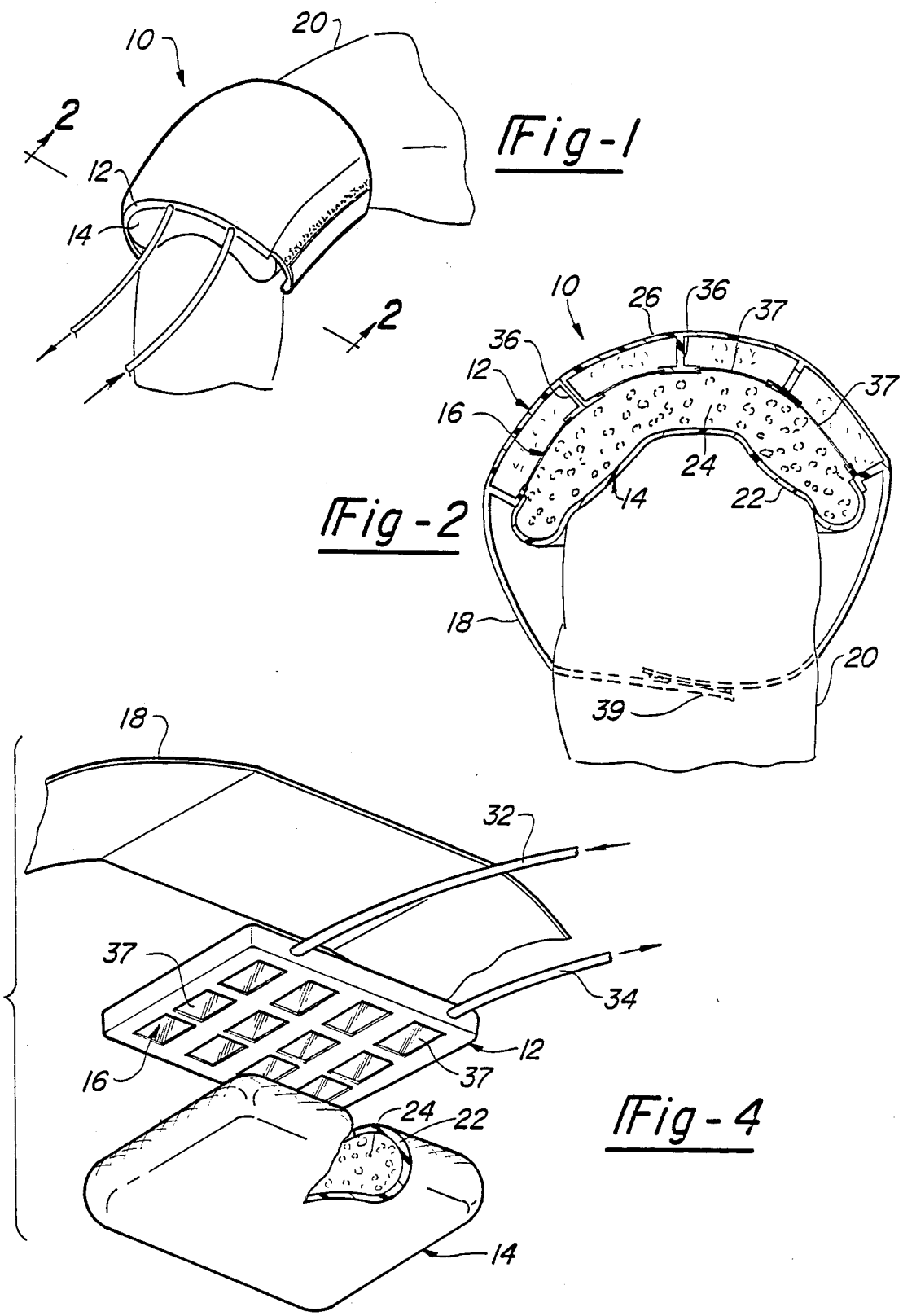

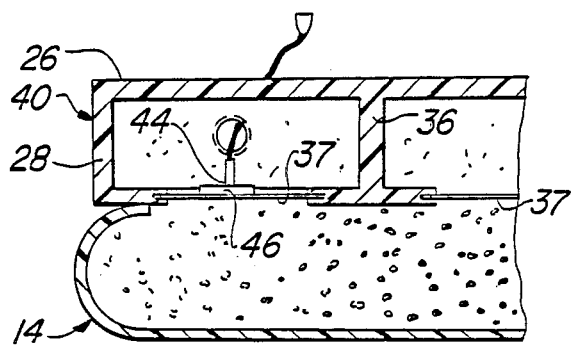
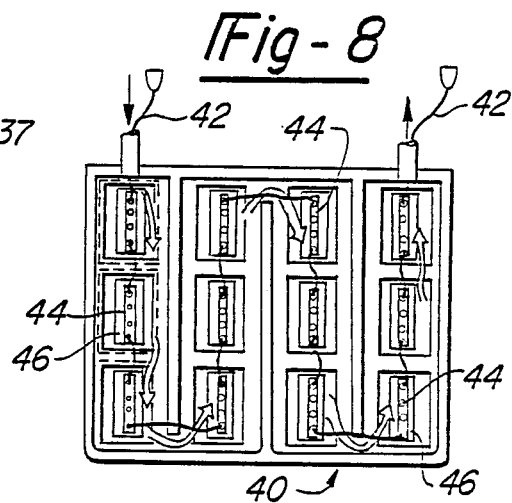
Fig-7
Fig-8
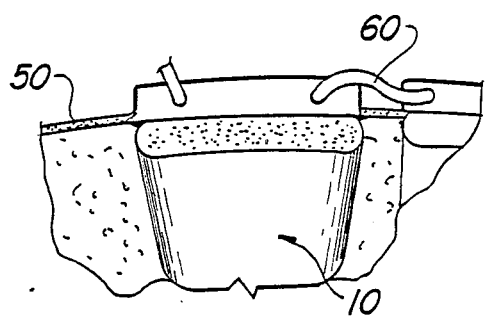
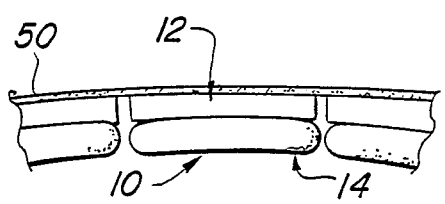
Fig-9
Fig-10
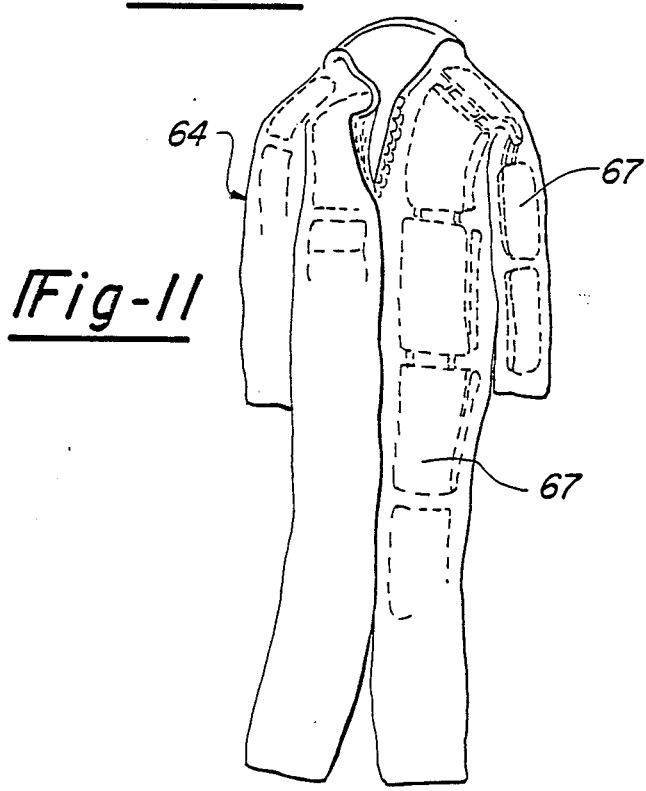
Fig-11

THERMAL BANDAGE

BACKGROUND OF THE INVENTION

The present invention relates to a thermal bandage for heating or cooling various portions of the human body and more particularly, to a thermal bandage which readily conforms to the contours of a body portion to maintain the adjacent skin at a predetermined uniform temperature to aid in healing and the like.

A number of thermal applicators exist in the prior art in which thermal fluid is circulated through the applicator to provide a continuous transfer of heat. Examples of this type of applicator are shown in U.S. Pat. Nos. 1,896,953; 2,726,658; and 3,683,902 which are incorporated by reference herein for teaching systems in which such applicator units may be used and for teaching thermal fluid storage and circulation means for such systems.

The above applicators, suffer from many shortcomings. Typically the applicators involve relatively thick bulk compresses which do not conform closely to the contour of the body. Failure of the compress to conform closely and to retain close contact once positioned, results in irregular heating and cooling of the skin area. This problem often results in irregular or nonuniform healing of the skin, swelling, and the like.

To overcome the above disadvantages the applicant of the present invention developed a bendable thermal pack unit disclosed in U.S. Pat. No. 4,108,146 which is included herein by reference. The disclosed invention provides a thermal pack unit which is configured to the general shape of the body portion to whch it is to be applied. This unit overcomes the earlier shortcomings by providing a thermal pack unit which conforms to the contour of the human body so that regular and uniform healing of the skin can be obtained. Further, the applicant of the present invention also developed another uniform cooling pack which is disclosed in U.S. Pat. No. 4,098,279 which is also incorporated by reference herein.

Although applicant's earilre bendable thermal pack unit possesses superior qualities and greatly improves over the prior art, it requires a different unit for each different body portion. It may be necessary to have numerous sizes of a specific bandage to cover the wide range of human sizes. Consequently, a doctor would have to have a huge inventory of different bandages for different anatomic sites and different sizes per site.

The present invention eliminates the deficiencies of the prior art and provides a simple, low cost, light weight thermal bandage which readily conforms to the contours of any portion of the human body to maintain uniform heating or cooling of the adjacent skin area.

BRIEF SUMMARY OF THE INVENTION

The present invention provides a thermal bandage which readily conforms to the contours of a portion of a human body to heat or cool adjacent skin areas. The bandage has a conforming member of supple heat conductive material adapted to readily conform to any contour of the body portion upon application to permit uniform distribution or extraction of heat. Further, the bandage includes a thermal pack mounted to the conformable member with means to either heat or cool the conforming member and therefore, the adjacent skin surface. Finally, the bandage includes a conductive surface separating the conforming member and thermal pack.

In the preferred embodiment, the heat conductive material includes a heat conductive fluid contained within a thin pliable outer material. The outer material is fixed about its perimeter to the thermal pack so that the fluid is in direct contact with the conductive surface. This provides the most efficient transfer of heat between the thermal pack and the conforming member. In addition to containing the fluid, the thin pliable outer material may also act as a sterile dressing to cover the adjacent skin portion to prevent infection. In a further embodiment, the conforming member is made of a heat conductive thermo-plastic material which is capable of readily conforming to the contour of the body portion.

The thermal pack of the preferred embodiment uses thermal fluid to heat or cool the conforming member, and it is flexible so that it can be bent to the general contours of the body portion. The pack includes a base, upstanding perimeter walls and a fluid flow chamber defined by the base, walls and conducting surface. The chamber has at least one separator which defines a circuitous flow path through the thermal pack. In this manner, either cooling fluid or heating fluid may be passed through the thermal pack along the flow path to provide uniform heat distribution to the skin area. In a further embodiment, the thermal pack employs thermo-electric means for heating and cooling.

The conducting plate of the preferred embodiment is constructed of a plurality of separate plates mounted to the thermal pack at the free ends of the perimeter walls and separators. All of the plates are substantially within the same plane with one surface of each plate being exposed to the thermal chamber and the opposite surface of each plate being in contact with the thermal conducting material. The conducting plate separates the thermal chamber from the conforming member and permits the transfer of heat between them. In a further embodiment, the conducting plate is constructed of a single flexible plate which functions in the same manner as the plurality of plates of the preferred embodiment.

BRIEF DESCRIPTION OF THE DRAWINGS

FIG. 1 is a perspective view of the thermal bandage of the present invention applied to a body portion.

FIG. 2 is a cross-sectional view taken along line 2—2 of FIG. 1.

FIG. 4 is a perspective exploded view of the thermal bandage of the present invention.

FIG. 7 is a partial cross-sectional side view of an alternative embodiment of the device.

FIG. 8 is a cut-away top view of the device of FIG. 7.

FIG. 9 is a partial perspective view of a further embodiment of the device.

FIG. 10 is a side view of the device illustrated in FIG. 9.

FIG. 11 is a perspective view of a garment employing the device of the present invention.

DETAILED DESCRIPTION OF THE INVENTION

Figure 3:
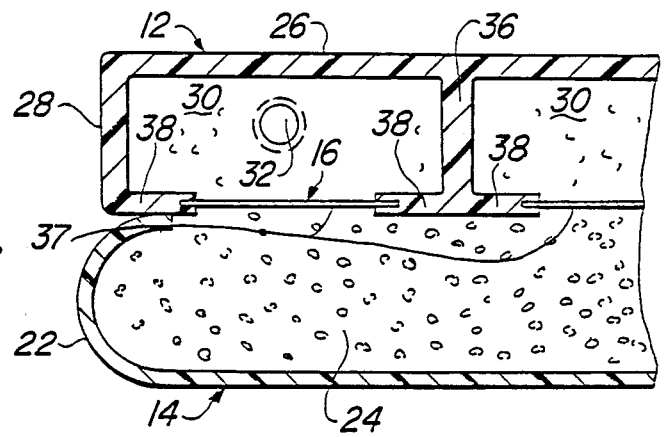
FIG. 3 is a partial cross-sectional view of the thermal bandage of FIG. 2.

With reference to FIG. 1, the thermal bandage of the present invention is indicated generally at 10 and, for purposes of illustration, is shown attached to a body portion 20 for thermal treatment of the adjacent skin area. To be effective, particularly in surgery, a thermal bandage must uniformly heat or cool a skin area, otherwise complications may arise, such as for example, swelling of the skin area or possible destruction of newly applied skin before the flow of blood to the skin can begin. The thermal bandage of the present invention provides the needed uniform heat transfer because of its ability to readily conform to the contours of the body portion.

Referring now to FIG. 2, thermal bandage 10 includes a conforming member 14 which is placed against the skin. A thermal pack 12 is mounted to member 14 to provide the necessary thermal change to heat or cool the adjacent skin area, and a thermal conducting surface 16, such as for example a pliable metal plate, is interposed between the conforming member 14 and the thermal pack 12 to separate them and to facilitate heat transfer between them. As is apparent from FIGS. 1 and 2, conforming member 14 readily conforms to the exact contour of the body portion to insure a uniform temperature across the skin. Further, thermal pack 12 and conducting surface 16 bend to retain contact between member 14 and the skin. As shown in FIG. 2, a strap 18 is provided to hold bandage 10 in place.

As shown in FIGS. 3–4, the conforming member 14 has a thin pliable outer material 22, such as for example, a fluid tight cloth or cellophane-type material that encloses a heat conductive substance 24 which can readily adapt to the shape of any object it contacts. Substance 24 may be, as for example, a glycol gel or liquid. The outer material 22 is connected along its free ends to the perimeter of thermal pack 12 by adhesive or the like so that the conductive substance 24 is in direct contact with conducting surface 16. In this way, the heat transferred through surface 16 is directly received by or extracted from substance 24.

In a further embodiment of the present invention, the heat conductive substance 24 comprises a heat conductive thermoplastic material which has the capability of readily conforming to the contours of the body portion. In this embodiment, the pliable outer material 22 is not necessary since the thermoplastic material is not in the fluid state; however, the outer material 22 can still be added and be used as a sterile dressing for the skin surface if desired. To further improve the thermal conductivity of the thermoplastic material, a metallic matrix may be interspersed within the thermoplastic.

Figure 5:
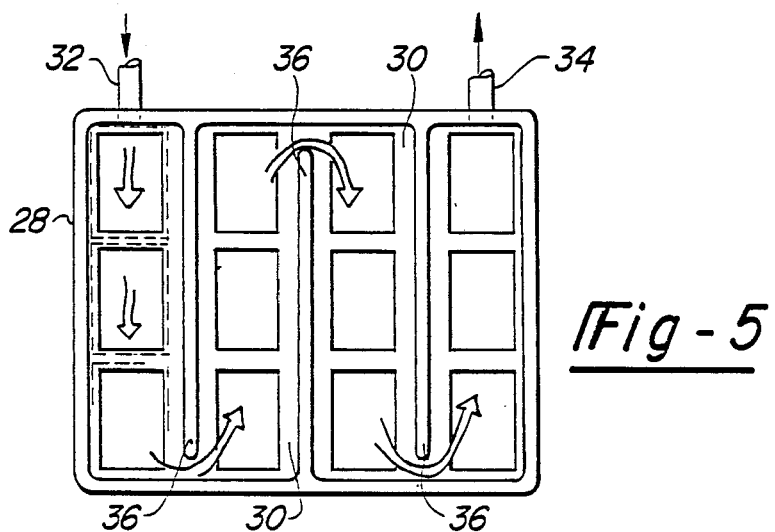
FIG. 5 is a cut-away top view of the thermal pack of the present invention illustrating the fluid flow path.

The thermal pack 12 of the preferred embodiment, see FIGS. 2, 3 and 5, is made of a durable plastic material such as polyvinyl which can be easily bent to the general shape of the body portion. Pack 12 includes a base 26, perimeter walls 28 and a fluid flow chamber 30 that is defined by walls 28, base 26 and conducting surface 16. Fluid is circulated within chamber 30 between an inlet tube 32 and an outlet tube 34. The circulating fluid is either hot or cold depending upon the application and continually flows over the conducting surface 16 to either transfer heat to or extract heat from conforming member 14. In this manner, with continuous thermal fluid flow, the adjacent skin area can be maintained at a uniform temperature. Various means are available for circulating and heating or cooling the fluid, as for example, a pump with a temperature control device and a fluid reservoir.

To provide for flow of thermal fluid across the entire surface of conducting medium 16, separators 36 are provided within chamber 30 to give the fluid flow a circuitous or serpentine path. Thus, due to separators 36 the fluid entering at inlet 32 must follow a predetermined path along conducting surface 16 so that the entire surface of conducting surface 16 is traversed by thermal fluid. As can be seen in FIG. 5, separators 36 form channels within chamber 30, alternately extending from opposed perimeter walls 28 leaving only a small opening between the free end of each separator 36 and the opposed wall 28 for the passage of fluid.

Figure 6:
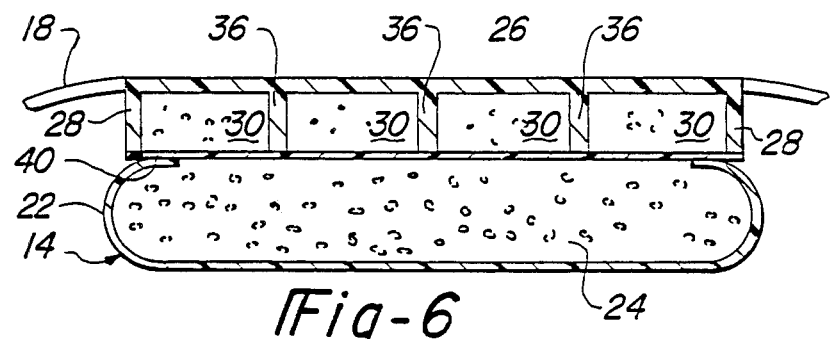
FIG. 6 is a cross-sectional side view of an alternative embodiment of the device.

The conducting surface 16 of the preferred embodiment is formed by a plurality of substantially equal sized metal squares 37 with each square being mounted within flanges 38 on the free ends of the perimeter walls 28 and separators 36. The mounting of the squares to flanges 38 completes the channel and prevents thermal fluid leakage. With reference to FIG. 6, a further embodiment of surface 16 is illustrated having a single flexible sheet 40 which is secured to the free ends of perimeter walls 28 and separators 36 by, as for example, an adhesive. Flexible sheet 40 may be made of a flexible metal such as aluminum.

In use, the thermal bandage 10 is placed against the body portion with the conforming member 14 in contact with the skin area. Strap 18 is wrapped around the body portion and fastened, as for example, by a Velcro-type fastener 39. (Velcro is a synthetic material which adheres when pressed together). The flexible thermal pack 12 and conducting surface 16 bend to the general shape of the body portion to assist in keeping the conforming member 14 in contact with the skin area. After bandage 10 is attached, a thermal fluid source is connected between inlet 32 and outlet 34 for circulating hot or cold fluid through thermal pack 12. In this manner, heat is either added to or extracted from the skin area.

Referring now to FIGS. 7 and 8, a further embodiment of the present invention is shown employing a thermo-electric pack 40. Preferably, pack 40 has a flexible base 26 with perimeter walls 28 and separators 36 for mounting conducting squares 37. A series of electrically interconnected electrodes 44 are mounted to squares 37. Insulators 46 are interposed between squares 37 and electrodes 44. An electrical lead 42 connects electrodes 44 with a power source (not shown). Upon energizing the power source, an electric current flows through each electrode 44 producing thermo-electric heat or cold flow which in turn raises or lowers the temperature of the conforming member 14. It is within the intended scope of this invention to use other thermo-electric devices to provide the necessary heating and cooling of the conforming member, such as, for example, a peltier device may be used which permits both heating and cooling by the use of dissimilar materials and electric current.

Because of the ability of conforming member 14 to readily adapt to any contour immediately upon contact, a standard bandage 10 as described above can be used for almost all applications. For example, a surgeon can use the standard thermal bandage 10 of the present invention to heat or cool a knee, joint, or body surface. Further, as illustrated in FIGS. 9 and 10, the versatility of the thermal bandage of the present invention allows the bandage to be manufactured and distributed on a sheet 50 from which bandages 10 may be removed. Preferably, sheet 50 is cut to remove a single bandage 10 or multiple bandages 10 if a larger skin area must be covered. Connectors 60 interconnect the individual bandages and when cut in the location between adjacent bandages, they form an inlet 32 and outlet 34 for fluid or the electrical leads 42, as described previously.

Referring now to FIG. 11, a thermal garment 64 is illustrated employing a plurality of thermal bandages 10. The garment 64 has a plurality of pockets or areas 67, shown in phantom, into which the thermal bandages can be placed. Garment 64 permits extremely large areas of the body to be thermally treated in a uniform manner. Preferably, the bandages 10 have thermo-electric packs which can be connected in series so that one electrical source can be used. This electrical source can be carried by the individual who can then move as desired. Further, a thermal pack using fluid can also be used.

With this detailed description of the thermal bandage of the present invention and the operation thereof, it will be obvious to those skilled in the art that various modifications can be made to the thermal bandage and in the materials and specific configurations used therein without departing from the spirit and scope of the present invention which is limited only by the appended claims.

What is claimed is:

1. A thermal bandage adapted to closely conform to the contours of a portion of a human body to heat or cool the adjacent skin area; said thermal bandage comprising:

a conforming member forming one side of said thermal bandage and including supple heat conducting material which readily conforms to the contour of said body portion such that said conforming member is in complete contact with said skin area permitting uniform distribution or extraction of heat from said skin area, and said conforming member including an outer thin pliable material surface which encloses said heat conducting material, and said outer pliable material surface having end portions;

a bendable thermal pack mounted to said conforming member and forming an opposite side of said thermal bandage, said thermal pack being coextensive with the conforming member and said pack having means to heat or cool said conforming member;

a single boundary layer heat conducting surface interposed between said conforming member and said pack to separate said thermal pack and said conforming member and to facilitate the conduction of heat thereacross;

said heat conducting material includes a first heat conductive fluid contained between said thin pliable outer material surface and said single boundary layer heat conducting surface, said pliable outer material being fixed at its end portions to said thermal pack such that said first heat conductive fluid is in contact with said heat conducting single boundary layer surface and only said conforming member contacts said skin area;

said heating or cooling means providing for the circulation of a second heat conductive fluid under pressure through said thermal pack and over said single boundary layer conducting surface to either transfer heat to or extract heat from said first heat conducting fluid; and means for holding said conforming member in contact with said skin area such that heat is either added to or extracted from the skin area.

2. The thermal bandage of claim 1, wherein said first heat conductive fluid is a heat conductive gel.

3. The thermal bandage of claim 1, wherein said thermal pack comprises a flexible housing and said means to heat or cool said conforming member includes upstanding walls about the perimeter of said housing defining a fluid flow chamber therebetween, at least one separator positioned within said flow chamber to define a circuitous fluid flow path and an inlet and an outlet for the circulation of the second heat condutive fluid into and out of said thermal pack along said flow path.

4. The thermal bandage of claim 1, wherein said thermal pack includes a housing having upstanding perimeter walls with said conducting surface and said conforming member being mounted to said walls.

5. The thermal bandage of claim 1, wherein said thermal pack includes a base with upstanding perimeter walls, said conducting surface being mounted to said walls to form a chamber therebetween for the circulation of the second heat conductive fluid, an inlet and an outlet for circulating said fluid through said chamber with said chamber including at least one separator to define a circuitous fluid path such that said fluid traverses substantially the entire surface area of said conducting surface.

6. The thermal bandage of claim 5, wherein said conducting surface is comprised of a plurality of conducting plates mounted to the free ends of said perimeter walls and said separators.

7. The thermal bandage of claim 5, wherein said conducting surface is comprised of a flexible heat conductive plate mounted to the free ends of said perimeter walls.

8. The thermal bandage as defined in claim 1 including a plurality of conforming members and bendable thermal packs and means for connecting said plurality of conforming members and thermal packs in a garment-like structure such that large areas of the body may be thermally treated in a uniform manner.

* * * * *